United States Patent [19]
Scherz

[11] 4,323,364
[45] Apr. 6, 1982

[54] METHOD OF AND APPARATUS FOR EXAMINING SUBSTANCES AND MIXTURES OF SUBSTANCES

[76] Inventor: Michael Scherz, Nietzschestr. 4, 6800 Mannheim 1, Fed. Rep. of Germany

[21] Appl. No.: 197,325

[22] Filed: Oct. 15, 1980

[30] Foreign Application Priority Data

Oct. 31, 1979 [DE] Fed. Rep. of Germany ....... 2943942

[51] Int. Cl.$^3$ ...................... G01N 27/30; G01N 9/30
[52] U.S. Cl. ................... 23/230 R; 422/68; 422/72; 204/1 T; 204/195 R
[58] Field of Search ............. 422/50, 68, 72; 204/1 T, 195 R; 23/230 R; 233/26

[56] References Cited
U.S. PATENT DOCUMENTS

| | | | |
|---|---|---|---|
| 3,684,450 | 8/1972 | Adler et al. | 422/72 X |
| 3,741,726 | 6/1973 | Mitchell et al. | 422/72 X |
| 3,770,027 | 11/1973 | Guigan | 422/72 X |
| 3,795,451 | 3/1974 | Mailen | 422/72 X |
| 4,204,917 | 5/1980 | Yamamoto et al. | 422/72 X |

Primary Examiner—Ronald Serwin
Attorney, Agent, or Firm—Wenderoth, Lind & Ponack

[57] ABSTRACT

A method of and apparatus for examining substances by subjecting them to a gravitational field while measuring the electrical effect derived from any resulting charge orientation. A centrifuge is preferably employed to give high g forces and an electrode system is used to provide an output signal. The output signal can be plotted against changing g forces to give a gravitational spectrum analysis graph. An apparatus for using such method is also described. Said apparatus comprises a direct or capacitive electrode system with one or more electrodes made of noble metal.

15 Claims, 4 Drawing Figures

METHOD OF AND APPARATUS FOR EXAMINING SUBSTANCES AND MIXTURES OF SUBSTANCES

The invention relates to a method of examining substances and mixtures of substances.

Many chemicals compounds and elements in which the atoms are arranged asymmetrically in the molecule have a permanent molecular electrical dipole moment. In the usual distribution, the dipole vectors are statistically distributed in all directions, so that no macroscopically detectable electrical charges or voltages are present. Such molecules and also molecules of some substances not having a permanent electrical dipole moment can be aligned as a whole or at least in their basic parts by gravitational force because of the mass-inertia of their basic parts.

The invention is aimed at solving the problem of providing a method of examining substances and mixtures of substances, taking into account deflection or alignment of the charge orientation under the effect of gravitational force.

According to one aspect of the invention there is provided a method of examining substances and mixtures of substances, the method consisting in taking the substance or mixture to be examined in a state in which gravitational orientation of molecules is possible, applying a specific gravitational field to the substance or mixture, and deriving an output signal in accordance with any deflection of the molecular charge orientation resulting from the application of the specific gravitational field. This general basic principle can be used extremely extensively for qualitative and quantitative analyses, for determining the structures of known and unknown substances, as well as for confirming or obtaining information on samples having material compositions of a like kind, for recording the progress of a chemical reaction, for identifying short-life intermediate products, etc. Basically, any substance or any mixture of substances as well as ideal and nonideal solutions can be subjected to such gravitation-spectral examination. In the present description, the terms "substance" and "mixture of substances" cover both liquid and gaseous substances including the combined states of aggregation, homogeneous and non-homogeneous mixtures of material in fluid or flowable form, as well as solid bodies, the molecules of which have a corresponding limited mobility.

The composition of the substances to be examined is not altered chemically or physically. On completion of the examination and after the gravitational field ceases, the examined substances will have suffered no material loss. Solid substances are expediently first dissolved in a suitable solvent.

The required effect of the gravitational field is expediently produced by centrifuging, particularly by high-speed centrifuging, and gravitational forces of such magnitude can be produced, particularly with the aid of a high-speed centrifuge, that high selectivity and specificity can be achieved in the examination. Another possible way of producing the gravitational field consists, for example, in suddenly slowing down the moved sample.

The required measured amount may advantageously be produced as an electrical voltage at suitable electrodes.

In a particularly advantageous form of the method, the change in the measured amount in dependence upon a progressive change in gravitational force can be represented as a gravitation spectrum. In this system, curves are obtained which comprise ascending legs and flats which can be associated with the orientation or alignment of the components of the molecule in the gravitational field.

A further advantage may be obtained by applying, further to the gravitational field, an electrical and/or magnetic additional field having a predetermined direction. Advantageously, this additional field may have at least one main component in the direction in which the dipoles are oriented under the effect of the gravitational field. An electrical and/or magnetic additional field of constant field-strength appears to be advantageous. The position and magnitude of the additional field may be expediently so determined by experiment that the required effect used for measuring or separation occurs to the optimum extent.

In the case of electrically conductive substances, a process of electrolysis can be advantageously initiated during the gravitational action by means of such electrical additional field. Thus for example, when separating radioactive mixtures of substances, it appears to be possible, during high-speed centrifuging, either to introduce certain constituents into the product to be separated off, or to prevent their entry into said product.

In a further expedient form of the method and for examining dissolved electrically conductive macromolecular substances, an electrophoresis process is carried out at least during the gravitational action. In the case of macromolecular systems, comprising proteins for example, in which sedimentation has previously been achieved by centrifuging or high-speed centrifuging, this form of the method offers the possibility of effecting a considerable improvement in the form of a sharper and higher resolution of the bands and of a marked saving in time in the centrifuging operation. In some circumstances, it is expedient to continue electrophoresis after completion of the gravitational action.

Instead of having a constant field-strength, the applied additional field may have a variable field-strength which, for example, varies over a predetermined time. This use of the electrical additional field is particularly suitable in the separation of colloidal systems during their preparation.

The above-described method is also of special importance when the composition of a substance or a mixture of substances is unknown. Information on constituents of a mixture as well as the identity of comparable substances can be obtained from correspondence of characteristics. Such examinations are of particular importance not only in science and industry, but also in medicine, since in the examination of body substances, for example, certain characteristic measured amounts or gravitation spectra occur for unknown substances, with which may be associated physiological processes as well as pathological conditions of varying degrees of severity.

According to another aspect of the invention there is provided apparatus for examining substances or mixtures of substances comprising a centrifuge which has at least one chamber for holding the substance or mixture to be examined and subjecting it to centrifugal gravitational forces, an electrode system for detecting changes in charge orientation in the substance and mixture, and an electrical output circuit for deriving an output signal from the electrode system. An arrangement comprising at least two spaced electrodes is preferred, and the use of more than two electrodes is of particular importance when electrical vectors occur in different directions after the gravitational force has taken effect. This may be advantageously reinforced by the additional electrical field.

Generally, the electrical measuring system is so designed that the measured amount, corresponding to the orientation of the molecular charges, is recorded as a function of the change in the gravitational field. In particular, voltage, current and charge can be determined directly or indirectly, for example photo-electrically, to provide the measured amount.

In one arrangement two oppositely disposed electrodes are directly connected into the circuit of the electrical measuring system by way of leads. In a further arrangement, the electrodes are considered as being the plates of a capacitor, the charge of which forms the input of the electrical measuring system. The electrodes may form the oppositely disposed wall surfaces of a centrifuge chamber made of insulating material. Advantageously, the electrodes are made of noble metal, for example, platinum or gold.

BRIEF DESCRIPTION OF THE DRAWINGS

With the aid of the drawings, the method of the invention will now be described in greater detail by reference to apparatus illustrated diagrammatically. In the drawings:

FIG. 1 illustrates diagrammatically a high-speed centrifuge which has two chambers 1, 2 having noble-metal electrodes 3, 4, 5, 6 on their walls. The electrodes 3, 4, 5, 6 are connected in series and to sliding contact rings 7, 8, the voltage of which is tapped by way of brushes 9, 10. A recording instrument 12 is connected by way of an amplifier 11, which instrument is also connected to a tachometer device 13 for emitting signals in accordance with the speed of the centrifuge shaft 15. Shaft 15 is driven by a motor 14.

Monochloromethane, dissolved in a suitable solvent, is put into the chambers 1, 2. This substance appears to be particularly suitable for use in the method on account of its permanent dipole moment. The centrifuge is then started up, and the speed n is slowly increased to approximately 20.000 r.p.m. (approximately 100,00 g). The voltage U is recorded as a function of the speed n by the instrument 12.

Figure 1:
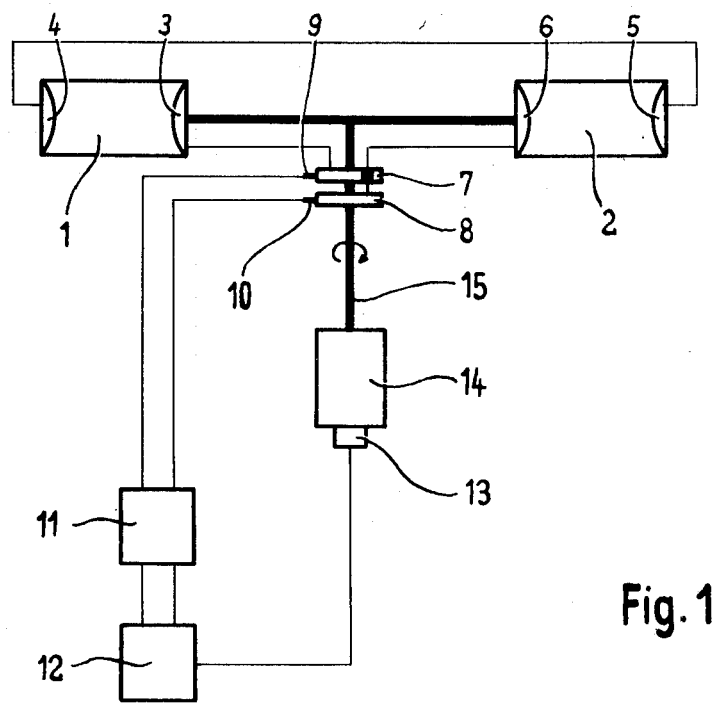
FIG. 1 illustrates in principle a high-speed centrifuge arrangement for performing the measuring method.
Figure 2:
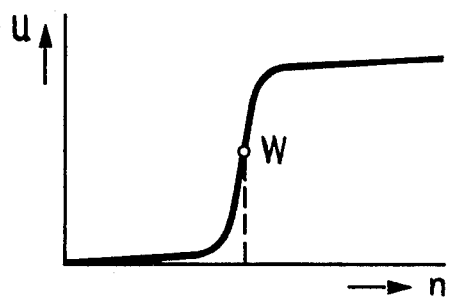
FIG. 2 shows a simple gravitation spectrum for detecting the presence of substances.

The S-shaped curve shown in FIG. 2 is obtained. The position of the turning point W is specific to the substance, assuming constant temperature and the use of a particular solvent, and it enables qualitative information regarding the composition of the material under examination to be obtained.

Quantitative information can likewise be arrived at from the voltage differences or the differences in other derived electrical measured amounts, e.g. current, which are achieved during the gravitational effect. If, for example, a single-molar solution gives a voltage of 0.6 mV, then with a ½ molar solution, a voltage of 0.3 mV occurs, and with a ¼ molar solution, a voltage of 0.15 mV. The method also enables information to be obtained regarding the direction of the examined dipole moment in the substance in question.

Figure 3:
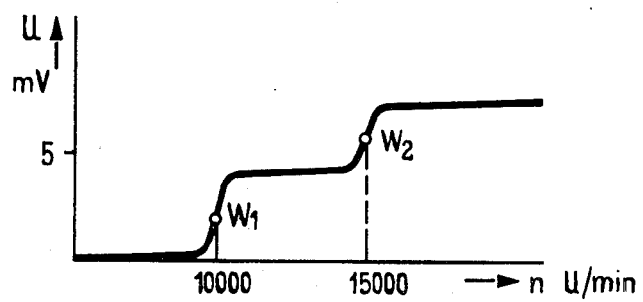
FIG. 3 shows a gravitation spectrum for detecting two components of a mixture of substances.

In the example to which FIG. 3 relates, various quantities of monochloromethane and monoiodomethane, i.e. likewise substances having a permanent electrical dipole moment, are dissolved in a suitable solvent. The mixture of substances is put into the chambers 1, 2.

The recording instrument 12 shows $U=f(n)$ during the centrifuging process.

Under the effect of the rising gravitation values, the asymmetrically structured molecules of the substances to be investigated become oriented and assume a preferential direction. Since the iodine atom is considerably heavier than the chlorine atom, first the monoiodomethane molecules and, thereafter, at a higher speed, the monochloromethane molecules become aligned and, in fact, in such a way that the halide atoms lie in the direction of the gravitational field.

The measurement results in a stepped curve with two S-shaped parts, and the change points $W_1$, $W_2$ of these S-shaped parts i.e. the middle points of the straight portions represent the value specific to the substances, at constant temperature and in a specific solvent, which value enables them to be identified, i.e. permits qualitative information to be obtained regarding the composition of one of the materials under examination.

Figure 4:
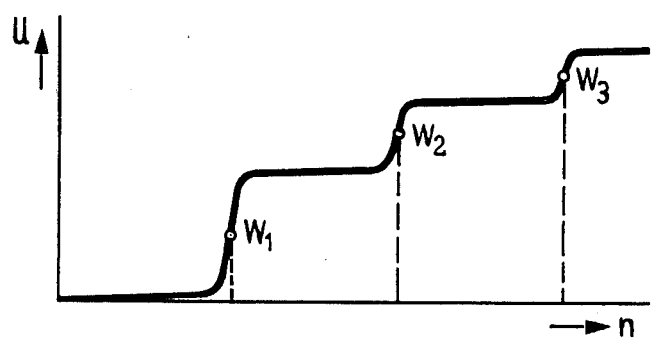
FIG. 4 shows a gravitation spectrum for detecting various iodine isotopes iodine compounds.

In the FIG. 4 example, monoiodomethane, dissolved in a suitable solvent and containing iodine in three different iodine isotopes in a predetermined mass ratio, was centrifuged under the previously described conditions but with a greater gravitational force. By means of the fine resolution of the spectrum thus obtainable, there results several S-shaped curve parts with adjacent flat sections. The positions of the characteristic change points ($W_1$, $W_2$, $W_3$) of the voltage curve can be seen in FIG. 4. The curve parts are the resultants of the isotope equilibrium present in the iodine compounds used. Because of the precise measuring facility and the clear allotment of a positive or a negative charge to the electrodes, the direction of the dipole moment vector can be determined spatially. Since the isotope equilibrium is known in most cases from other measurements, it is possible, on the basis of the gravitation spectrogram, to arrive at information as to which constituent of the molecule lies in the direction of the gravitational field. The heavy isotope, which generally occurs in a concentration different from that of the lighter isotope, is the first to become aligned.

By means of such measurements and taking into consideration the natural proportions of isotope mixtures, it is possible to observe the structures of unknown as well as known substances. An initially unknown substance can be determined in a mixture by recording curves suited to the natural isotope equilibrium, of a particular atom. The recording of two gravitational spectra of mixtures of substances enables information to be obtained regarding the similarity of the mixtures of substances, even when their composition is not known, simply on the basis of an identical gravitation spectrum.

What I claim is:

1. A method of examining substances and mixtures of substances, the method consisting in taking the substance or mixture to be examined in a state in which gravitational orientation of molecules is possible, applying a specific gravitational field to the substance or mixture, and deriving an output signal in accordance with any deflection of the molecular charge orientation resulting from the application of the specific gravitational field.

2. A method according to claim 1, wherein the size of the applied gravitational field is above 20 g.

3. A method according to claim 1, wherein the substance to be examined is dissolved in a solvent.

4. A method according to claim 1, wherein the effect of the gravitational field is produced by centrifuging.

5. A method according to claim 1, wherein the output signal in relation to a variable specific gravitational field is presented as a gravitational spectrum.

6. A method according to claim 1, wherein the measured amount is the voltage produced from charge deviation.

7. A method according to claim 1, wherein further to the gravitational field, an additional electric and/or magnetic field having a predetermined direction is applied.

8. A method according to claim 7, wherein the additional field has at least one main component in the direction in which the molecular charges are deflected under the effect of the gravitational field.

9. A method according to claim 7 or claim 8, wherein the additional field has a field strength which is constant with time.

10. A method according to claim 1, wherein in the case of dissolved macromolecular electrically conductive substances, an electrophoresis process is carried out during the gravitational action.

11. Apparatus for examining substances and mixtures of substances comprising a centrifuge which has at least one chamber for holding the substance or mixture to be examined and subjecting it to centrifugal gravitational forces, an electrode system for detecting changes in the substance and mixture, and an electric output circuit for deriving an output signal from the electrode system.

12. Apparatus according to claim 11, wherein two oppositely disposed electrodes are connected directly into the output circuit of the electrical measuring system by leads.

13. Apparatus according to claim 11, wherein the electrode system forms a capacitor, the charge of which forms the input of the electrical output circuit.

14. Apparatus according to claim 11, wherein the electrode system has one or more electrodes made of noble metal.

15. Apparatus according to claim 12, wherein the electrodes form the oppositely disposed wall surfaces of the chamber which is otherwise made of insulating material.

* * * * *